(12) United States Patent
Offenbacher et al.

(10) Patent No.: US 6,214,185 B1
(45) Date of Patent: Apr. 10, 2001

(54) SENSOR WITH PVC COVER MEMBRANE

(75) Inventors: Helmut Offenbacher; Bernhard Peter Harald Schaffar; Nicole Wiedner, all of Graz; Gabriela Pestitschek, Feldkirchen; Andreas Martin Dolezal, Graz, all of (AT)

(73) Assignee: AVL Medical Instruments, Schaffhausen (CH)

( * ) Notice: Subject to any disclaimer, the term of this patent is extended or adjusted under 35 U.S.C. 154(b) by 0 days.

(21) Appl. No.: 09/061,524

(22) Filed: Apr. 16, 1998

(30) Foreign Application Priority Data

Apr. 17, 1997 (AT) ........................................................ 664/97

(51) Int. Cl.$^7$ .................................................... C12M 1/40
(52) U.S. Cl. ......................... 204/403; 204/415; 205/778; 435/287.9; 435/288.7
(58) Field of Search ..................................... 204/403, 415, 204/416, 418; 205/198, 777.5, 778, 792, 793; 435/287.2, 287.9, 817, 288.7

(56) References Cited

U.S. PATENT DOCUMENTS

| | | | |
|---|---|---|---|
| 4,757,022 | * | 7/1988 | Shults et al. ........................ 204/415 |
| 4,966,671 | * | 10/1990 | Nylander et al. ..................... 204/418 |
| 4,981,570 | * | 1/1991 | Yamaguchi et al. .................. 204/418 |
| 5,078,856 | * | 1/1992 | Yamaguchi et al. .................. 204/418 |
| 5,312,537 | * | 5/1994 | Harrison et al. ..................... 204/416 |
| 5,417,835 | * | 5/1995 | Brown et al. ........................ 204/403 |
| 5,522,977 | * | 6/1996 | Shieh ................................. 204/403 |
| 5,540,828 | | 7/1996 | Yacynych . |
| 5,547,561 | * | 8/1996 | Vadgama et al. .................... 204/403 |
| 5,607,567 | * | 3/1997 | Yun et al. ............................ 204/418 |
| 5,645,710 | * | 7/1997 | Shieh ................................. 204/403 |
| 5,840,168 | * | 11/1998 | Chaniotakis et al. ................ 204/416 |

FOREIGN PATENT DOCUMENTS

| | | | |
|---|---|---|---|
| 0 503 943 | * | 9/1992 | (EP) . |
| 603154A2 | | 12/1993 | (EP) . |
| 0707064 | | 4/1996 | (EP) . |
| 1415597 | | 11/1975 | (GB) . |
| 59-11183 | * | 1/1984 | (JP) . |
| 9213271 | | 8/1992 | (WO) . |

OTHER PUBLICATIONS

"A Fast Responding Fibre Optic Glucose Biosensor Based on an Oxygen Optrode", Bernhard P.H. Schaffar and Otto S. Wolfbeis, *Biosensors& Bioelectronics*, vol. 5, pp. 137–148 (1990).

"Optimisation of Poly(vinyl chloride) Matrix Membrane Ion–Selective Electrodes for Ammonium Ions", Analyst, Mar. 1988, vol. 113, pp. 497–500.

"Poly(vinyl chloride), Polysulfone and Sulfonated Poly-ether–ether Sulfone Composite Membranes for Glucose and Hydrogen Peroxide Perm–Selectivity in Amperometric Biosensors", Analyst, Apr. 1996, vol. 121, pp. 521–526.

"New Polymeric Membrane Materials for Fabricating Potentiometric Ions and Bioselective Sensors", Polymeric Materials Science and Engineering, pp. 292–293, (1991).

\* cited by examiner

*Primary Examiner*—William H. Beisner
(74) *Attorney, Agent, or Firm*—Baker Botts L.L.P.

(57) ABSTRACT

The invention is concerned with a sensor for the determination of the concentration and the detection of an enzyme substrate in a liquid sample, the sensor comprising an enzyme capable of reacting with the enzyme substrate while producing a substance directly or indirectly detectable, a detection device for this substance and a cover membrane from a polymer permeable to the enzyme substrate, characterized in that the polymer is a polyvinyl chloride copolymer, i.e. a copolymer from vinyl chloride and a further monomer, the copolymer comprising hydrophilic groups. The sensor according to the invention may be provided as an optical sensor or as an amperometric sensor.

18 Claims, 1 Drawing Sheet

SENSOR WITH PVC COVER MEMBRANE

The present invention is concerned with a sensor (biosensor) for the determination of the concentration and the detection of an enzyme substrate in a liquid sample, which sensor comprises an enzyme capable of reacting with said enzyme substrate while producing a substance directly or indirectly detectable, a detection device and a cover membrane or cover layer from a polymer permeable to the enzyme substrate.

BACKGROUND OF THE INVENTION

Today, sensors provided as amperometric sensors or enzyme electrodes or as optical sensors (optodes) are widely used to determine the amount of or to detect certain substances such as glucose, oxygen, $CO_2$, in the blood and in other body liquids.

The construction and the function of an amperometric enzyme electrode is known for example from EP-A 0 603 154 of the applicant. The construction and the function of an optode is known for instance from Biosensors & Bioelectronics 5(1990) pp 137–148.

Amperometric sensors for the determination of glucose, lactate or creatinine are preferably constructed with oxidoreductases and a detection device to determine hydrogen peroxide (base electrode). They function in such a way that the oxidase such as glucose oxidase, lactate oxidase and sarcosin oxidase oxidizes the analyte to be determined with oxygen to the correspondent oxidation product and hydrogen peroxide, the concentration of hydrogen peroxide produced being proportional to the concentration of the analyte and being measured by anodic oxidation at approximately 650 mV versus Ag/AgCl at stainless steel or carbon electrodes (base electrodes). Alternatively, measuring may also be carried out at electrodes having a catalytical effect such as platinized carbon and mangane dioxide, at a reduced oxidation voltage (approximately 300 mV).

Further possibilities of determination are measuring the oxygen consumption or using mediators which may be measured by oxidation at the electrode instead of the hydrogen peroxide and also serve, in an oxidized form, as a substitute for oxygen.

The classical amperometric sensor comprises four layers: a base electrode, an interference-blocking layer, an enzyme layer and a cover membrane or cover layer respectively. This construction is schematically shown in the attached FIG. 1, reference number 1 indicating an electroconductive layer, e.g. from silver, applied onto a support (not shown). The base electrode 2 is applied onto the electroconductive layer 1. On top of the base electrode 2, the interference-blocking layer 3, the enzyme layer 4 and the cover membrane 5 are provided. The cover membrane 5 is in contact with the sample.

The interference-blocking layer 3 of an amperometric sensor serves to keep away from the electrode any electroactive substances of the sample such as paracetamole, uric acid, ascorbic acid, which may be oxidized directly at the electrode surface and thus show wrong, excessive signals. As the interference-blocking layer, layers from cellulose acetate and polyphenylene diamine are of preferred use, the polyphenylene diamine layer being produced by polymerisation of phenylene diamine directly onto the base electrode. Unplasticised polyvinyl chloride (PVC) and nafion may also be applied directly from their solution.

As the cover layer 5, a polycarbonate membrane made microporous by etching is frequently used, the pore width typically being 0.03 $\mu$m at a porosity of less than 5%. This cover membrane is biocompatible and limits diffusion due to its reduced porosity, but does not prevent enzymes from being transported through the pores. To improve the diffusion properties, this layer is frequently laminated and/or additionally coated. By wetting with hydrophobe plasticisers, a so-called supported liquid membrane may be prepared.

A cover layer 5 of a porous polycarbonate membrane has the drawback of being incapable of sufficiently protecting the underlying enzyme layer 4 from proteases. Moreover, it is incapable of preventing the washing out of enzymes from the enzyme layer 4, since enzymes are capable of diffusing through pores 0.03 $\mu$m wide.

Cover layers are often mechanically attached to the enzyme layer. When the cover layer is combined with the enzyme layer, this layer has to be mechanically attached to the base electrode. Such mechanical attachments are expensive, technically complex and frequently cause problems insofar as it is difficult to apply the membrane onto the underlying layer without producing air bubbles. This usually restricts the constructive freedom when designing sensors, since an embossed electrode surface is required to attach a membrane under mechanical tension to the electrode. The tension required frequently causes fissures and creases. Additionally, sheet membranes are relatively thick, and therefore the sensors produced have comparatively low electric currents and long response times.

To prepare the cover membrane it is further known to apply a solution of the polymer onto the enzyme layer and to evaporate the solvent. Thus for example, cover membranes of nafion, PVC, polyurethane, silicone, polyacrylate (p-HEMA) and cellulose acetate which stick to the underlying layer without any mechanical attachment, i.e. only by adhesion, may be prepared.

The polymers used so far which may be applied directly from their solution onto the enzyme layer or the electrode include only a few, such as nafion and cellulose acetate, which are selective towards electrochemically active interferents. Additionally, many polymers are soluble only in volatile, aggressive or toxic solvents, such as cellulose acetate in DMSO and acetone, and PVC in tetrahydrofurane and cyclohexanone. This circumstance is relevant for the production process as well as for safety reasons. It is also relevant for the electrode itself, since plastic portions may be deteriorated or enzymes present in the enzyme layer may be destroyed by these solvents. From plasticised PVC, plasticisers may diffuse into surrounding plastic portions or into the enzyme layer.

Another drawback consists in that in most polymers, particularly in plasticised PVC, permeability to the analytes such as glucose or lactate may be adjusted only by varying the layer thickness, since permeability is primarily due to faults in the membrane and the porosity thus produced. Even slight differences in the layer thickness may cause a total loss in permeability.

SUMMARY OF THE INVENTION

It is the object of the present invention to overcome the drawbacks cited above in a sensor mentioned above and in particular to provide a sensor wherein it is not necessary to mechanically attach the cover layer. Moreover, when applying the cover layer from the solution, none of the aggressive, toxic or extremely volatile solvents used in the state of the art are to be employed.

The sensor according to the invention for the determination of the concentration and the detection of an enzyme substrate in a liquid sample, which sensor comprises an enzyme capable of reacting with said enzyme substrate while producing a substance directly or indirectly detectable, a detection device and a cover membrane of a polymer permeable to the enzyme substrate is characterised in that said polymer is a polyvinyl chloride copolymer, i.e. a copolymer of vinyl chloride and a further monomer, which copolymer comprises hydrophilic groups. The copolymer used according to the invention to prepare the cover membrane may be a block copolymer, an alternating copolymer or a random copolymer.

As the hydrophilic groups, hydroxy, ester and/or carboxyl groups, are preferred.

The PVC copolymer used according to the invention is easily soluble in high-boiling esters. This permits an automatized discharge for several hours. In contrast, pure PVC is usually dissolved in tetrahydrofurane, which due to its high volatility does not permit a reproducible, automatized mass production.

A further advantage is that the dissolved polymer may be applied from this solution directly onto the enzyme layer. Inactivation of the enzyme layer caused by the cover layer according to the invention is virtually impossible, since compared to sensors not covered only about half of the signal will be lost. It is remarkable however that the linearity of the sensor is multiplied. A comparable cover membrane such as one made from nafion shows a similar signal loss but does not significantly increase the linearity of the sensor.

The copolymer used according to the invention is preferably made of vinyl chloride and one or more from vinyl alcohol, vinyl ester such as vinyl acetate, vinyl hydroxy ester such as hydroxypropyl acrylate and vinyl carboxylic acids such as maleic acid. Exemplary PVC copolymers are poly-(vinyl chloride-co-vinyl acetate), poly-(vinyl chloride-co-vinyl acetate-co-2-hydroxypropyl acrylate, poly-(vinyl chloride-co-vinyl acetate-co-maleic acid and poly-(vinyl chloride-co-vinyl acetate-co-vinyl alcohol).

A particular embodiment of the sensor according to the invention is characterized in that the further monomer wherefrom the polyvinyl chloride copolymer is made is vinyl acetate and/or maleic acid.

The further monomer is preferably contained in the copolymer in an amount of from 5 to 35% by mass, particularly from 10 to 20% by mass, based on the mass of vinyl chloride.

A further preferred embodiment of the sensor according to the invention consists in that the cover membrane contains a hydrophilic plasticiser. As the plasticiser, dextrane, glycerin, polyethylenglycol or glycols have shown good results.

Via addition of the plasticiser it is possible to exactly adjust the permeability. In an amperometric sensor, the addition of e.g. 3% by mass of glycerin increases the sensor signal e.g. to lactate by 100% while simultaneously increasing linearity by approximately 10% with an identical layer thickness. Even when applied in an optical sensor, the measuring range will be significantly increased after applying the cover membrane according to the invention.

In comparison with a cover membrane made of pure PVC, the cover membrane according to the invention made of the PVC copolymer permits a significantly better adjustment of permeability to glucose, since due to the hydrophilic copolymer component there is a priori a better permeability to glucose. It has been found that when the layer thickness is doubled the signal intensity will drop not more than by half, whereas a cover membrane made from pure PVC may suffer a total permeability loss when the layer thickness is doubled.

The cover membrane according to the invention impedes washing out of the enzymes or other components of the enzyme layer, thus increasing the lifetime of the sensor. The lifetime of a lactate sensor could be increased e.g. from 1.5 days (without cover membrane) to 14 days (with cover membrane).

Conveniently, the plasticiser is contained in an amount of from 0.5 to 5% by mass, based on the polyvinyl chloride copolymer.

The sensor according to the invention may be provided as an enzyme electrode, the detection device being a base electrode.

In this case, the cover membrane may be applied directly, i.e. without any intermediate interference-blocking membrane, onto the base electrode or onto a layer containing the enzyme. This is possible because the cover membrane according to the invention both increases the linearity of the sensor due to an improved diffusion inhibition and locks out electroactive interferents. Using the cover membrane according to the invention, the influence of 1 mmol/l of paracetamol could be lowered from 1.4 mmol/l of lactate without cover membrane to 0.2 mmol/l of lactate. Also, linearity of the sensor (a ratio of measured values at 5 and 12 mmol/l of lactate means absolute linearity) increased from 1.1 to 2.2.

The cover membrane may stick by adhesion to the base electrode or to the layer containing the enzyme. It need not be applied onto the base electrode or onto the layer containing the enzyme as a film in a mechanical way.

Further, the sensor according to the invention may be provided as an optical sensor.

The invention is also concerned with a method for the determination of the concentration and the detection of an enzyme substrate in a liquid sample by means of a sensor contacted with the liquid sample, which method is characterized in that a sensor according to the invention is employed.

The invention is further concerned with the use of a polyvinyl chloride copolymer comprising hydrophilic groups to prepare the cover membrane of a sensor.

BRIEF DESCRIPTION OF THE DRAWINGS

By means of the attached drawings, preferred embodiments of the invention are described in more detail.

DETAILED DESCRIPTION OF THE PREFERRED EMBODIMENT

Figure 1:
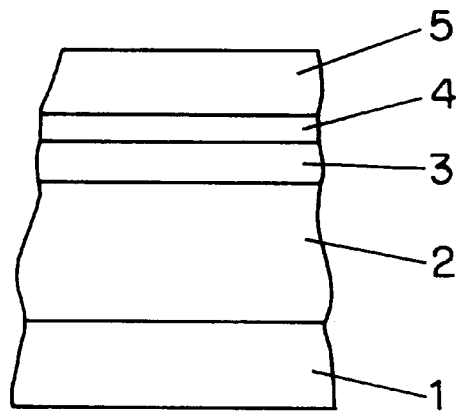
FIG. 1 is a schematic illustration of a classical ampermotric sensor FIGS. 2 and 3 schematically show a cross-section of an enzyme electrode according to the invention and an optical sensor (optode) according to the invention respectively.
Figure 2:
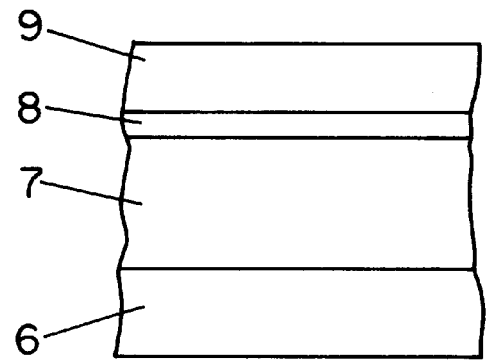

FIG. 2 shows the configuration of a preferred embodiment of an enzyme electrode according to the invention, reference number 6 referring to an electroconductive layer, e.g. from silver, applied onto a plastic support (not shown). The base electrode 7 is applied onto layer 6. On top of the base electrode 7, the enzyme layer 8 and the cover membrane 9 according to the invention which is in contact with the sample are provided. The layer structure of such an enzyme electrode may be built up as follows:

First silver strip conductors for the reference electrode, the counter electrode and the enzyme electrode according to the invention (base electrode or working electrode respectively) are printed on a plastic support.

Further, the reference electrode is prepared from an Ag/AgCl paste in the sensing area. The counter electrodes are additionally coated with a carbon paste in the sensing area. As the base for the enzyme electrode, a mixture of 5% of $MnO_2$ in a carbon paste is printed in the sensing area. Thereupon a drop of a 10% solution of glucose oxidase in water or alternatively in a bathotonic polyacryl matrix is applied.

Thereafter the cover membrane is prepared by applying, one after the other, one to three drops of a 1–3% solution of the polyvinyl chloride copolymer according to the invention such as PVC-co-vinylacetate-maleinate in butoxyethyl acetate and evaporating the solvent.

To improve permeability and to prevent a possible crystallisation in the polyvinyl chloride copolymer membrane, hydrophilic plasticisers (glycerin, PEG, dextrane or the like) may be added, conveniently in a concentration of 3% of the polyvinyl chloride copolymer.

Instead of the glucose oxidase, other enzymes for the determination of other substrates, such as lactate oxidase for the determination of lactate, may also be employed.

Figure 3:
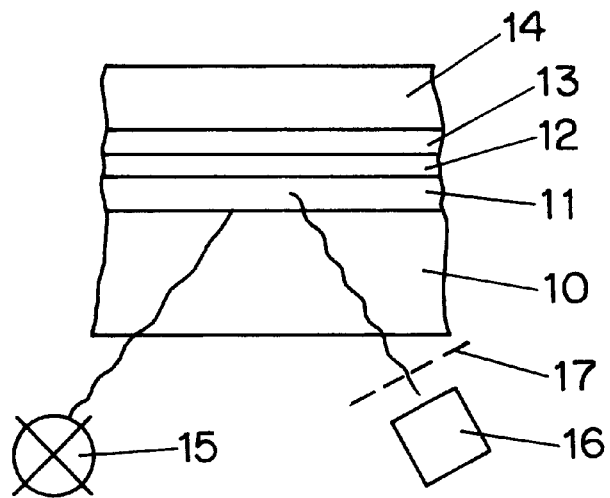

FIG. 3 schematically shows the configuration of an optical sensor wherein reference number 10 refers to a support, made e.g. from polyester, reference number 11 refers to a silicone layer containing an indicator such as decacyclene for the detection of oxygen, reference number 12 indicates a layer of finely divided carbon for optical isolation and reference number 13 indicates an enzyme layer (gel layer). The preparation of such a sensor is known e.g. from Biosensors & Bioelectronics 5(1990), pp. 137–148.

To apply the cover membrane 14 of polyvinyl chloride copolymer it is proceeded as above described. This cover layer 14 is in contact with the sample.

The substance to be determined such as glucose penetrates through the cover membrane 14 into the enzyme layer 13 containing glucose oxidase. The oxygen produced by enzymatic oxidation of glucose penetrates into the indicator layer 11 and quenches the fluorescence of decacyclene produced by means of an exciting device 15 emitting exciting light into the silicone layer 11. From the decrease of fluorescence it is possible to deduce, by means of a measuring device 16 in front of which a filter 17 is provided, the oxygen concentration and subsequently the glucose concentration, in a substantially known manner.

What is claimed is:

1. A sensor for the determination of the concentration and the detection of an enzyme substrate in a liquid sample, said sensor comprising:
    an enzyme layer comprising an enzyme capable of reacting with said enzyme substrate while producing a substance directly or indirectly detectable;
    a detection device; and
    a cover membrane covering the enzyme layer comprising a polymer permeable to said enzyme substrate wherein said polymer is a polyvinyl chloride copolymer prepared from vinyl chloride and a further monomer, said copolymer comprising hydrophilic groups.

2. A sensor according to claim 1 wherein said hydrophilic groups are selected from the group consisting of hydroxy, ester, carboxyl groups and combinations thereof.

3. A sensor according to claim 2, wherein said further monomer is at least one selected from the group consisting of vinyl alcohol, vinyl ester, vinyl hydroxyl ester and vinyl carboxylic acids.

4. A sensor according to claim 3, wherein said further monomer is at least one selected from the group consisting of vinyl acetate and maleic acid.

5. A sensor according to any one of claims 1, 2, 3, or 4 wherein said further monomer is incorporated into said copolymer in an amount of 5 to 35% by weight based on the weight of vinyl chloride incorporated in said copolymer.

6. A sensor according to claim 5 wherein said cover membrane further comprises a hydrophilic plasticizer.

7. A sensor according to claim 6 wherein said hydrophilic plasticizer is selected from the group consisting of dextrane, glycerine, polyethylene glycol and glycols.

8. A sensor according to claim 7 wherein said plasticizer is present in an amount of 0.5 to 5% by weight based upon the polyvinyl chloride copolymer.

9. A sensor according to claim 6 wherein said plasticizer is present in an amount of 0.5 to 5% by weight based upon the polyvinyl chloride copolymer.

10. A sensor according to any one of claim 1, 2, 3 or 4 wherein said cover membrane further comprises a hydrophilic plasticizer.

11. A sensor according to claim 10, wherein said hydrophilic plasticizer is selected from the group consisting of dextrane, glycerin, polyethylene glycol and glycols.

12. A sensor according to claim 10 wherein said plasticizer is present in an amount of 0.5 to 5% by weight based on the polyvinyl chloride copolymer.

13. A method for the determination and the detection of an enzyme substrate in a liquid sample comprising the steps of:
    providing a sensor in accordance with any one of claim 1, 2, 3, or 4;
    contacting said sensor with said liquid sample and,
    determining and detecting the presence of said enzyme substrate in said sample with said detection device.

14. A sensor for the determination of the concentration and detection of an enzyme substrate in a liquid sample, said sensor comprising:
    an enzyme layer comprising an enzyme capable of reacting with said enzyme substrate while producing a substance directly or indirectly detectable,
    a base electrode for detecting said substance; and
    a cover membrane covering the enzyme layer comprising a polymer permeable to said enzyme substrate wherein said polymer is a polyvinyl chloride copolymer prepared from vinyl chloride and a firther monomer and wherein said copolymer comprises hydrophilic groups.

15. A sensor according to claim 14 wherein said cover membrane is adjacent to and in contact with said base electrode.

16. A sensor according to claim 15 wherein said cover membrane attaches by adhesion to said base electrode.

17. An optical sensor for the determination of the concentration and detection of an enzyme substrate in a liquid sample comprising:
    an enzyme layer comprising an enzyme capable of reacting with said enzyme substrate while producing a substance which reacts with an indicator;
    an optical isolation layer;
    a detection layer comprising said indicator; and
    a cover membrane covering the enzyme layer comprising a polymer permeable to said enzyme substrate, said polymer comprising a copolymer prepared from vinyl chloride and a further monomer and wherein said copolymer comprises hydrophilic groups.

18. An optical sensor according to claim 17 wherein said indicator is decacyclene.

\* \* \* \* \*